US010765149B2

(12) United States Patent
Reevell

(10) Patent No.: US 10,765,149 B2
(45) Date of Patent: Sep. 8, 2020

(54) AEROSOL-GENERATING SYSTEM HAVING VARIABLE AIRFLOW

(71) Applicant: Altria Client Services LLC, Richmond, VA (US)

(72) Inventor: Tony Reevell, London (GB)

(73) Assignee: Altria Client Services LLC, Richmond, VA (US)

(*) Notice: Subject to any disclaimer, the term of this patent is extended or adjusted under 35 U.S.C. 154(b) by 169 days.

(21) Appl. No.: 15/812,057

(22) Filed: Nov. 14, 2017

(65) Prior Publication Data
US 2018/0132534 A1    May 17, 2018

Related U.S. Application Data

(63) Continuation of application No. PCT/EP2017/078151, filed on Nov. 3, 2017.

(30) Foreign Application Priority Data

Nov. 14, 2016  (EP) .................................. 16198749

(51) Int. Cl.
*A24F 47/00*  (2020.01)
*A61M 15/06*  (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
None
See application file for complete search history.

(56) References Cited

U.S. PATENT DOCUMENTS 2,124,130 A * 7/1938 Van Deventer ......... A24F 13/06
131/198.2
2,967,528 A * 1/1961 Kelter ..................... A24F 13/04
131/198.2
(Continued)

FOREIGN PATENT DOCUMENTS

CN     103960785 A    8/2014
EP       2891415 A2   7/2015
(Continued)

OTHER PUBLICATIONS

Written Opinion for Application No. PCT/EP2017/078151 dated Feb. 1, 2018.
(Continued)

*Primary Examiner* — Thor S Campbell
(74) *Attorney, Agent, or Firm* — Harness, Dickey & Pierce, P.L.C.

(57) ABSTRACT

An aerosol-generating system may include a cartridge, a vaporiser section configured to receive the cartridge, and a power supply section configured to supply electrical power to the vaporiser section. The cartridge may include a cartridge housing containing a solid aerosol-forming substrate and defining a cartridge air inlet that extends through a wall portion of the cartridge housing. The vaporiser section may include a vaporiser housing containing an electric heater and a liquid aerosol-forming substrate and defining a vaporiser air outlet that extends through a wall portion of the vaporiser housing. The cartridge wall portion is configured to abut the vaporiser wall portion when the cartridge is received within the vaporiser section. The cartridge configured to be rotatable with respect to the vaporiser section to vary the amount of overlap between the cartridge air inlet and the vaporiser air outlet.

14 Claims, 4 Drawing Sheets

(51) Int. Cl.
*A61M 11/04* (2006.01)
*A61M 11/00* (2006.01)

(52) U.S. Cl.
CPC ... *A61M 11/003* (2014.02); *A61M 2205/3653* (2013.01); *A61M 2205/8206* (2013.01)

(56) References Cited

U.S. PATENT DOCUMENTS

| | | | | |
|---|---|---|---|---|
| 3,270,751 | A * | 9/1966 | Tucker | A24F 13/04 |
| | | | | 131/198.2 |
| 3,713,452 | A * | 1/1973 | D'Elia | A24F 13/06 |
| | | | | 131/198.2 |
| 4,848,375 | A | 7/1989 | Patron et al. | |
| 4,922,901 | A * | 5/1990 | Brooks | A24F 47/006 |
| | | | | 128/202.27 |
| 4,947,875 | A * | 8/1990 | Brooks | A24F 47/006 |
| | | | | 128/202.21 |
| 2008/0092912 | A1* | 4/2008 | Robinson | H05B 3/42 |
| | | | | 131/200 |
| 2013/0014772 | A1 | 1/2013 | Liu | |
| 2013/0160764 | A1* | 6/2013 | Liu | A24F 47/008 |
| | | | | 128/202.21 |
| 2013/0192620 | A1* | 8/2013 | Tucker | A61M 11/003 |
| | | | | 131/329 |
| 2013/0333700 | A1 | 12/2013 | Buchberger | |
| 2014/0261486 | A1* | 9/2014 | Potter | A24F 47/008 |
| | | | | 131/328 |
| 2014/0311505 | A1 | 10/2014 | Liu | |
| 2014/0353856 | A1* | 12/2014 | Dubief | B01F 3/04078 |
| | | | | 261/128 |
| 2014/0373856 | A1* | 12/2014 | Zuber | A24F 47/008 |
| | | | | 131/328 |
| 2015/0027454 | A1* | 1/2015 | Li | A24F 47/008 |
| | | | | 131/328 |
| 2015/0136155 | A1 | 5/2015 | Verleur et al. | |
| 2015/0173417 | A1 | 6/2015 | Gennrich et al. | |
| 2015/0173422 | A1 | 6/2015 | Liu | |
| 2015/0181928 | A1 | 7/2015 | Liu | |
| 2015/0189920 | A1 | 7/2015 | Liu | |
| 2015/0223522 | A1* | 8/2015 | Ampolini | A61M 11/042 |
| | | | | 131/328 |
| 2016/0007649 | A1* | 1/2016 | Sampson | A24F 13/02 |
| | | | | 131/187 |
| 2016/0143354 | A1* | 5/2016 | Liu | A24F 47/008 |
| | | | | 131/329 |
| 2016/0235121 | A1* | 8/2016 | Rogan | A24D 3/041 |
| 2017/0258138 | A1* | 9/2017 | Rostami | A61M 11/042 |
| 2017/0325505 | A1* | 11/2017 | Force | A24F 47/008 |
| 2017/0340014 | A1* | 11/2017 | Batista | F22B 1/284 |
| 2018/0070641 | A1* | 3/2018 | Batista | A61M 15/0036 |
| 2018/0160732 | A1* | 6/2018 | Bless | H05B 1/0244 |
| 2018/0168231 | A1* | 6/2018 | Reevell | A61M 15/0003 |
| 2018/0256834 | A1* | 9/2018 | Hepworth | A24F 47/002 |
| 2018/0338531 | A1* | 11/2018 | Reevell | A24F 47/008 |
| 2018/0360123 | A1* | 12/2018 | Silvestrini | A24B 15/167 |
| 2019/0082739 | A1* | 3/2019 | Slivestrini | A24F 47/008 |
| 2019/0281891 | A1* | 9/2019 | Hejazi | A24B 13/02 |

FOREIGN PATENT DOCUMENTS

| | | |
|---|---|---|
| WO | WO-2013083636 A1 | 6/2013 |
| WO | WO-2014/195859 A2 | 12/2014 |
| WO | WO-2015/052192 A1 | 4/2015 |
| WO | WO-2015179388 A1 | 11/2015 |
| WO | WO-2015180058 A1 | 12/2015 |
| WO | WO-2015180061 A1 | 12/2015 |
| WO | WO-2016135342 A2 | 9/2016 |

OTHER PUBLICATIONS

Extended European Search Report #16198749.0 dated May 16, 2017.
Martinne Geller. "British American to Test Tobacco/E-Cigarette Hybrid". Thomson Reuters. Nov. 18, 2015. http://www.reuters.com/article/us-brit-am-tobacco-products-idUSKCN0T71U020151118 <https://protect-us.mimecast.com/s/LL6dBvfk86vhM>.
"HVS: The Next Generation Hybrid Vaping and New Way of Consume Tobacco". Jinjia Technologies. 2009-2014. http://jinjiatech.com/PRODUCTS/Heat/91 <https://protect-us.mimecast.com/s/GWJNBKiQ6NGfa>.
Written Opinion for corresponding PCT Application No. PCT/EP2017/078151 dated Nov. 13, 2018.
International Preliminary Report on Patentability for Corresponding Application No. PCT/EP2017/078151 dated Jan. 31, 2019.

* cited by examiner

US 10,765,149 B2

AEROSOL-GENERATING SYSTEM HAVING VARIABLE AIRFLOW

CROSS-REFERENCE TO RELATED APPLICATIONS

This is a continuation of and claims priority to PCT/EP2017/078151, filed on Nov. 3, 2017, and further claims priority to EP 16198749.0, filed on Nov. 14, 2016, both of which are hereby incorporated by reference in their entirety.

BACKGROUND

Field

Example embodiments relate to an aerosol-generating system (which may also be referred to as an electronic vaping system) configured to allow variable airflow through the system. The system may be in a form of an electrically operated smoking system.

Description of Related Art

An aerosol-generating system in a form of an electrically operated smoking system may comprise an aerosol-generating device comprising a battery, control electronics, and an electric heater for heating an aerosol-forming substrate. The aerosol-forming substrate may be contained within the aerosol-generating device. For example, the aerosol-generating device may comprise a liquid storage portion in which a liquid aerosol-forming substrate, such as a nicotine solution, is stored. Some devices have attempted to include a tobacco-based substrate to impart a tobacco taste to the generated aerosol. However, such devices typically are not amenable to customization.

SUMMARY

An aerosol-generating system may comprise a cartridge comprising a cartridge housing containing a solid aerosol-forming substrate, the cartridge housing defining a cartridge air inlet and a cartridge air outlet, the cartridge air inlet extending through a cartridge wall portion of the cartridge housing; a vaporiser section configured to receive the cartridge, the vaporiser section comprising a vaporiser housing containing an electric heater and a liquid aerosol-forming substrate, the vaporiser housing defining a vaporiser air inlet and a vaporiser air outlet, the vaporiser air outlet extending through a vaporiser wall portion of the vaporiser housing, the cartridge wall portion abutting the vaporiser wall portion when the cartridge is received within the vaporiser section, the cartridge configured to be rotatable with respect to the vaporiser section to vary an amount of overlap between the cartridge air inlet and the vaporiser air outlet; and a power supply section comprising a power supply configured to supply electrical power to the electric heater.

The vaporiser housing may defines a cavity configured to receive an upstream end of the cartridge housing.

The cartridge wall portion may be an upstream end wall of the cartridge housing, and the vaporiser wall portion may be an upstream end wall of the cavity.

The upstream end of the cartridge housing and the cavity may each have a circular cross-sectional shape.

The upstream end of the cartridge housing and the cavity may each have a polygonal cross-sectional shape.

Each of the vaporiser air outlet and the cartridge air inlet may have a semi-circular shape.

The cartridge housing may define a first compartment and a second compartment, the solid aerosol-forming substrate is within the first compartment, and the cartridge air inlet is in a form of a first cartridge air inlet in fluidic communication with the first compartment and a second cartridge air inlet in fluidic communication with the second compartment.

The cartridge may further comprise a second aerosol-forming substrate within the second compartment.

The second aerosol-forming substrate may comprise a flavourant.

The cartridge may be configured to be rotatable with respect to the vaporiser section to vary the amount of overlap between the vaporiser air outlet and each of the first cartridge air inlet and the second cartridge air inlet.

The cartridge may be configured so that the amount of overlap between the vaporiser air outlet and the first cartridge air inlet increases as the amount of overlap between the vaporiser air outlet and the second cartridge air inlet decreases.

Each of the vaporiser air outlet, the first cartridge air inlet, and the second cartridge air inlet may have a semi-circular shape.

The aerosol-generating system may further comprise a first indicium on an outer surface of the cartridge housing; and a second indicium on an outer surface of the vaporiser housing, wherein the first indicium and the second indicium are configured to cooperate to indicate a rotational orientation of the cartridge with respect to the vaporiser section.

The solid aerosol-forming substrate may comprise tobacco.

The liquid aerosol-forming substrate may comprise a nicotine-containing liquid.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
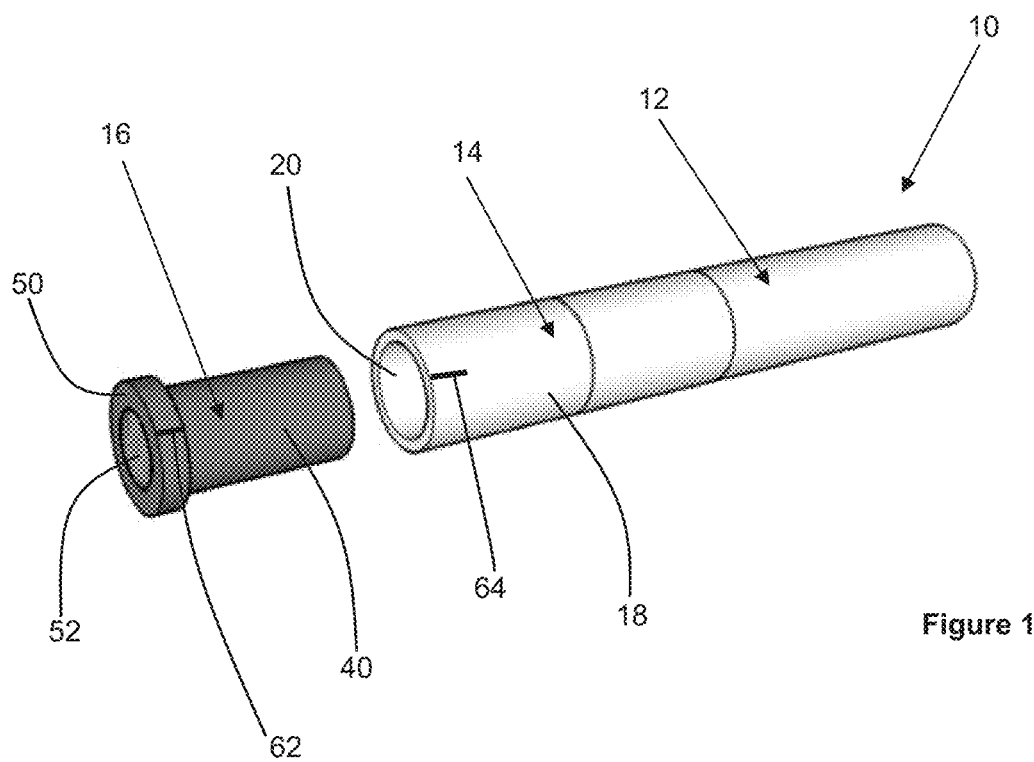
FIG. 1 is a first perspective view of an aerosol-generating system according to an example embodiment.
Figure 2:
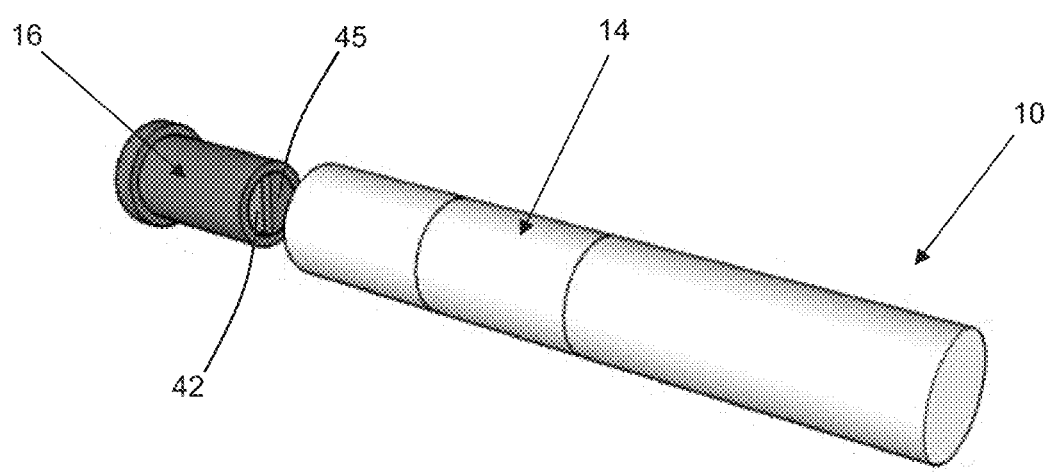
FIG. 2 is a second perspective view of the aerosol-generating system of FIG. 1.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

In the following description, illustrative embodiments may be described with reference to acts and symbolic representations of operations (e.g., in the form of flow charts, flow diagrams, data flow diagrams, structure diagrams, block diagrams, etc.) that may be implemented as program modules or functional processes including routines, programs, objects, components, data structures, etc., that perform particular tasks or implement particular abstract data types. The operations be implemented using existing hardware in existing electronic systems, such as one or more microprocessors, Central Processing Units (CPUs), digital signal processors (DSPs), application-specific-integrated-circuits (ASICs), SoCs, field programmable gate arrays (FPGAs), computers, or the like.

One or more example embodiments may be (or include) hardware, firmware, hardware executing software, or any combination thereof. Such hardware may include one or more microprocessors, CPUs, SoCs, DSPs, ASICs, FPGAs, computers, or the like, configured as special purpose machines to perform the functions described herein as well as any other well-known functions of these elements. In at least some cases, CPUs, SoCs, DSPs, ASICs and FPGAs may generally be referred to as processing circuits, processors and/or microprocessors.

Although processes may be described with regard to sequential operations, many of the operations may be performed in parallel, concurrently or simultaneously. In addition, the order of the operations may be re-arranged. A process may be terminated when its operations are completed, but may also have additional steps not included in the figure. A process may correspond to a method, function, procedure, subroutine, subprogram, etc. When a process corresponds to a function, its termination may correspond to a return of the function to the calling function or the main function.

As disclosed herein, the term "storage medium", "computer readable storage medium" or "non-transitory computer readable storage medium," may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, at least some portions of example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, processor(s), processing circuit(s), or processing unit(s) may be programmed to perform the necessary tasks, thereby being transformed into special purpose processor(s) or computer(s).

A code segment may represent a procedure, function, subprogram, program, routine, subroutine, module, software package, class, or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded, or transmitted via any suitable means including memory sharing, message passing, token passing, network transmission, etc.

According to some example embodiments, there is provided an aerosol-generating system (which may also be referred to as an electronic vaping system) comprising a cartridge, a vaporiser section, and a power supply section. The cartridge comprises a cartridge housing defining a cartridge air inlet and a cartridge air outlet, the cartridge air inlet extending through a wall portion of the cartridge housing. The cartridge also comprises a solid aerosol-forming substrate positioned within the cartridge housing. The vaporiser section comprises a vaporiser housing defining a vaporiser air inlet and a vaporiser air outlet, the vaporiser air outlet extending through a wall portion of the vaporiser housing. The vaporiser housing is configured to receive at least a portion of the cartridge. The vaporiser section also comprises an electric heater and a liquid aerosol-forming substrate each positioned within the vaporiser housing. The cartridge and the vaporiser section are configured so that the cartridge housing wall portion abuts the vaporiser housing wall portion when the vaporiser section receives the cartridge. A rotational orientation of the cartridge with respect to the vaporiser section is variable, the amount of overlap between the cartridge air inlet and the vaporiser air outlet being variable between different rotational orientations. The power supply section comprises a power supply for supplying electrical power to the electric heater.

As used herein, the term "aerosol-forming substrate" is used to describe a substrate capable of releasing volatile compounds, which can form an aerosol. The aerosols generated from aerosol-forming substrates of aerosol-generating systems may be visible or invisible and may include vapours (for example, fine particles of substances, which are in a gaseous state, that are ordinarily liquid or solid at room temperature) as well as gases and liquid droplets of condensed vapours.

Aerosol-generating systems may facilitate a variation of the airflow through the aerosol-generating system. Variation of the airflow may vary the resistance to draw of the aerosol-generating system. Variation of the airflow through the aerosol-generating system may vary a ratio of airflow through the solid-aerosol-forming substrate to airflow bypassing the solid-aerosol-forming substrate. A variation of airflow through the aerosol-generating system facilitates customisation of the vaping experience.

The aerosol-generating system may have a resistance to draw that is variable between about 60 and about 120 millimetres water gauge.

The vaporiser housing may define a cavity for receiving an upstream end of the cartridge housing. Providing a cavity for receiving an upstream end of the cartridge housing may facilitate engagement of the cartridge with the vaporiser section. The cavity may retain the cartridge in engagement with the vaporiser section during use of the aerosol-generating system. The cavity and the upstream end of the cartridge housing may be sized so that the upstream end of the cartridge housing is retained in the cavity by an interference fit during use of the aerosol-generating system.

The cross-sectional shape of the cavity may be substantially the same as the cross-sectional shape of the upstream end of the cartridge housing.

The cavity is configured to receive the upstream end of the cartridge housing in a plurality of rotational orientations of the cartridge with respect to the vaporiser section. The amount of overlap between the cartridge air inlet and the vaporiser air outlet in each rotational orientation of the cartridge is different from the amount of overlap between the cartridge air inlet and the vaporiser air outlet in at least one of the other rotational orientations of the cartridge. In an example embodiment, the amount of overlap between the cartridge air inlet and the vaporiser air outlet in each rotational orientation of the cartridge is different from the amount of overlap between the cartridge air inlet and the vaporiser air outlet in each of the other rotational orientations of the cartridge.

There is substantially no overlap between the cartridge air inlet and the vaporiser air outlet in at least one of the rotational orientations of the cartridge. Providing a rotational orientation in which there is substantially no overlap between the cartridge air inlet and the vaporiser air outlet may substantially hinder or prevent airflow through the aerosol-generating system when the aerosol-generating system is not in use.

The cartridge housing wall portion forms an upstream end wall of the cartridge housing and the vaporiser housing wall portion forms an upstream end wall of the cavity. When the upstream end of the cartridge housing is received within the cavity, the upstream end wall of the cartridge housing abuts the upstream end wall of the cavity. Abutting the two upstream end walls ensures that airflow from the vaporiser air outlet can only flow directly into the cartridge air inlet. This may ensure a direct correlation between the amount of overlap between the cartridge air inlet and the vaporiser air outlet, and the resistance to draw of the aerosol-generating system. In example embodiments in which there is substantially no overlap between the cartridge air inlet and the vaporiser air outlet in at least one rotational orientation of the cartridge with respect to the vaporiser section, abutting the two upstream end walls may facilitate the hindrance or prevention of airflow through the aerosol-generating system.

The upstream end of the cartridge housing and the cavity may each have a circular cross-sectional shape so that the rotational orientation of the cartridge with respect to the vaporiser section is continuously variable.

Providing the upstream end of the cartridge housing and the cavity with a circular cross-sectional shape may allow variation of the rotational orientation of the cartridge without removing the upstream end of the cartridge housing from the cavity.

Providing a continuously variable rotational orientation of the cartridge with respect to the vaporiser section may provide the aerosol-generating system with a continuous variation of resistance to draw between a maximum resistance to draw and a minimum resistance to draw. The maximum resistance to draw may occur when the amount of overlap between the cartridge air inlet and the vaporiser air outlet is at a minimum. The minimum resistance to draw may occur when the amount of overlap between the cartridge air inlet and the vaporiser air outlet is at a maximum.

The upstream end of the cartridge housing and the cavity may each have a polygonal cross-sectional shape to define a plurality of discrete rotational orientations of the cartridge with respect to the vaporiser. A plurality of discrete rotational orientations may correspond to a plurality of discrete and desired or predetermined resistance to draw values for the aerosol-generating system.

Each of the cartridge air inlet and the vaporiser air outlet may have any suitable size and shape. The cartridge air inlet and the vaporiser air outlet may have substantially the same size and shape. The cartridge air inlet may have at least one of a different size and a different shape compared to the vaporiser air outlet.

Each of the vaporiser air outlet and the cartridge air inlet may have a semi-circular shape. A semi-circular vaporiser air outlet and a semi-circular cartridge air inlet may be beneficial in example embodiments in which the upstream end of the cartridge housing and the cavity each has a circular cross-sectional shape. The combination of a semi-circular vaporiser air outlet and a semi-circular cartridge air inlet may provide the maximum amount of overlap between the vaporiser air outlet and the cartridge air inlet while retaining a rotational orientation in which there may be substantially no overlap between the vaporiser air inlet and the cartridge air outlet.

The cartridge housing may define a single compartment in which the solid-aerosol-forming substrate is positioned.

The cartridge housing may define a first compartment and a second compartment, wherein the solid-aerosol-forming substrate is positioned within the first compartment, and wherein the cartridge air inlet comprises a first cartridge air inlet in fluidic communication with the first compartment and a second cartridge air inlet in fluidic communication with the second compartment. The second compartment in combination with second cartridge air inlet may provide a second airflow path through the cartridge that bypasses the solid aerosol-forming substrate positioned within the first compartment.

The cartridge air outlet may comprise a first cartridge air outlet in fluidic communication with the first compartment and a second cartridge air outlet in fluidic communication with the second compartment. The first cartridge air inlet may be positioned at the upstream end of the cartridge housing and the first cartridge air outlet may be positioned at a downstream end of the cartridge housing so that the first cartridge air inlet and the first cartridge air outlet are in fluidic communication with each other via the first compartment. The second cartridge air inlet is positioned at the upstream end of the cartridge housing and the second cartridge air outlet is positioned at the downstream end of the cartridge housing so that the second cartridge air inlet and the second cartridge air outlet are in fluidic communication with each other via the second compartment.

The aerosol-generating system is configured so that the amount of overlap between the vaporiser air outlet and each of the first cartridge air inlet and the second cartridge air inlet is variable between different rotational orientations of the cartridge with respect to the vaporiser section. The aerosol-generating system is configured so that the amount of overlap between the vaporiser air outlet and the first cartridge air inlet increases as the amount of overlap between the vaporiser air outlet and the second cartridge air inlet decreases. The aerosol-generating system is configured so that the amount of overlap between the vaporiser air outlet and the second cartridge air inlet increases as the amount of overlap between the vaporiser air outlet and the first cartridge air inlet decreases. Such an arrangement allows a ratio of the amount of airflow through the first compartment to the amount of airflow through the second compartment to be changed.

Each of the vaporiser air outlet, the first cartridge air inlet, and the second cartridge air inlet may have a semi-circular shape. This may be beneficial in example embodiments in which the upstream end of the cartridge housing and the cavity each has a circular cross-sectional shape. Such an arrangement may facilitate continuous variation of the airflow through the aerosol-generating system between a configuration in which all of the airflow through the system is via the first compartment and a configuration in which all of the airflow through the system is via the second compartment. Between each of these configurations the airflow through the system may be divided between the first and second compartments. As the rotational orientation of the cartridge is varied, the amount of overlap between the vaporiser air outlet and the first cartridge air inlet is inversely proportional to the amount of overlap between the vaporiser air outlet and the second cartridge air inlet.

The vaporiser air outlet may have a semi-circular shape and each of the first cartridge air inlet and the second cartridge air inlet may have a quarter-circular shape. This configuration may be substantially as described in connection with the previously described example embodiment in which each of the first and second cartridge air inlets is semi-circular. Providing a semi-circular vaporiser outlet in combination with quarter-circular first and second cartridge air inlets allows for rotational orientations of the cartridge in which part or all of the first cartridge air inlet overlaps the vaporiser air outlet and none of the second cartridge air inlet overlaps the vaporiser air outlet. Providing a semi-circular vaporiser outlet in combination with quarter-circular first and second cartridge air inlets allows for rotational orientations of the cartridge in which part or all of the second cartridge air inlet overlaps the vaporiser air outlet and none of the first cartridge air inlet overlaps the vaporiser air outlet. Providing a semi-circular vaporiser outlet in combination with quarter-circular first and second cartridge air inlets allows for a rotational orientation of the cartridge in which the vaporiser air outlet does not overlap either of the first and second cartridge air inlets.

The second compartment may be a bypass compartment to provide an airflow pathway that bypasses the solid aerosol-forming substrate. This may allow the ratio of volatile compounds from the liquid aerosol-forming substrate to volatile compounds from the solid aerosol-forming substrate that is delivered from the aerosol-generating system to be varied. For example, decreasing the amount of overlap between the first cartridge air inlet and the vaporiser air outlet, and increasing the amount of overlap between the second cartridge air inlet and the vaporiser air outlet, may decrease the amount of volatile compounds delivered from the solid aerosol-forming substrate compared to the amount of volatile compounds delivered from the liquid aerosol-forming substrate.

The second compartment may be substantially empty. The second air inlet may be smaller than the first air inlet to accommodate a lower resistance to draw of the second compartment compared to the first compartment.

The cartridge may comprise a filter material positioned within the second compartment.

The cartridge may comprise a second aerosol-forming substrate positioned within the second compartment. This may allow the ratio of volatile compounds from the solid aerosol-forming substrate to volatile compounds from the second aerosol-forming substrate that is delivered from the aerosol-generating system to be varied. This arrangement may allow a flavour profile delivered by the aerosol-generating system to be varied. Thus, the amount of flavour delivered from the solid aerosol-forming substrate compared to the amount of flavour delivered from the second aerosol-forming substrate may be varied.

The second aerosol-forming substrate may comprise a second liquid aerosol-forming substrate. The second aerosol-forming substrate may comprise a second solid-aerosol-forming substrate.

Each of the liquid aerosol-forming substrate, the solid aerosol-forming substrate, and, where present, the second aerosol-forming substrate may comprise a flavourant. The flavourant may comprise menthol.

The aerosol-generating system may further comprise a first indicium provided on an outer surface of the cartridge housing and a second indicium provided on an outer surface of the vaporiser housing, wherein the first indicium and the second indicium cooperate to indicate the rotational orientation of the cartridge with respect to the vaporiser section. This may assist the setting of a desired rotational orientation of the cartridge with respect to the vaporiser section.

The vaporiser section may comprise a porous carrier material, wherein the liquid aerosol-forming substrate is provided on the porous carrier material. Providing the liquid aerosol-forming substrate on a porous carrier material may reduce the risk of the liquid aerosol-forming substrate leaking from the vaporiser section.

The porous carrier material may comprise any suitable material or combination of materials which is permeable to the liquid aerosol-forming substrate and allows the liquid aerosol-forming substrate to migrate through the porous carrier material. The material or combination of materials is inert with respect to the liquid aerosol-forming substrate. The porous carrier material may or may not be a capillary material. The porous carrier material may comprise a hydrophilic material to improve distribution and spread of the liquid aerosol-forming substrate. This may assist with consistent aerosol formation. The particular material or materials will depend on the physical properties of the liquid aerosol-forming substrate. Examples of suitable materials are a capillary material, for example a sponge or foam material, ceramic- or graphite-based materials in the form of fibres or sintered powders, a foamed metal or plastics material, a fibrous material, for example made of spun or extruded fibres, such as cellulose acetate, polyester, or bonded polyolefin, polyethylene, terylene or polypropylene fibres, nylon fibres or ceramic. The porous carrier material may have any suitable porosity so as to be used with different liquid physical properties.

The solid aerosol-forming substrate may comprise tobacco. The solid aerosol-forming substrate may comprise a tobacco-containing material containing volatile tobacco flavour compounds which are released from the substrate upon heating.

The solid aerosol-forming substrate may comprise tobacco containing deprotonated nicotine. Deprotonating the nicotine within tobacco may increase the volatility of the nicotine. Nicotine may be deprotonated by subjecting the tobacco to an alkalising treatment.

The solid aerosol-forming substrate may comprise a non-tobacco material. The solid aerosol-forming substrate may comprise tobacco-containing material and non-tobacco containing material.

The solid aerosol-forming substrate may include at least one aerosol-former. As used herein, the term "aerosol former" is used to describe any suitable known compound or mixture of compounds that, in use, facilitates formation of an aerosol. Suitable aerosol-formers include, but are not limited to polyhydric alcohols, such as propylene glycol, triethylene glycol, 1,3-butanediol, and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate In an example embodiment, the aerosol formers are polyhydric alcohols or mixtures thereof, such as propylene glycol, triethylene glycol, 1,3-butanediol, and glycerine.

The solid aerosol-forming substrate may comprise a single aerosol former. Alternatively, the solid aerosol-forming substrate may comprise a combination of two or more aerosol formers.

The solid aerosol-forming substrate may have an aerosol former content of greater than 5 percent on a dry weight basis.

The solid aerosol-forming substrate may have an aerosol former content of between approximately 5 percent and approximately 30 percent on a dry weight basis.

The solid aerosol-forming substrate may have an aerosol former content of approximately 20 percent on a dry weight basis.

The liquid aerosol-forming substrate may comprise a tobacco-containing material comprising volatile tobacco flavour compounds which are released from the liquid upon heating. The liquid aerosol-forming substrate may comprise a non-tobacco material. The liquid aerosol-forming substrate may include water, solvents, ethanol, plant extracts and natural or artificial flavours. The liquid aerosol-forming substrate may comprise an aerosol former. Suitable aerosol formers include polyhydric alcohols or mixtures thereof, such as propylene glycol, triethylene glycol, 1,3-butanediol, and glycerine.

The liquid aerosol-forming substrate may comprise nicotine.

The liquid aerosol-forming substrate may be free from nicotine. In such example embodiments, the vaporised liquid aerosol-forming substrate may be drawn through the solid aerosol-forming substrate during use to strip one or more volatile compounds from the solid aerosol-forming substrate. The vaporised liquid aerosol-forming substrate may strip nicotine from the solid-aerosol-forming substrate. A solid aerosol-forming substrate comprising tobacco containing deprotonated nicotine may be particularly suited to embodiments in which the liquid aerosol-forming substrate is free from nicotine.

Where present, the second aerosol-forming substrate may comprise any of the solid and liquid aerosol-forming substrates described herein. The composition of the second aerosol-forming substrate may be different from the composition of each of the liquid and solid-aerosol-forming substrates.

The electric heater may comprise a resistive heating coil.

The electric heater may comprise a resistive heating mesh.

The resistive heating mesh may comprise a plurality of electrically conductive filaments. The electrically conductive filaments may be substantially flat. As used herein, "substantially flat" means formed in a single plane and not wrapped around or otherwise conformed to fit a curved or other non-planar shape. A flat heating mesh can be easily handled during manufacture and provides for a robust construction.

The electrically conductive filaments may define interstices between the filaments and the interstices may have a width of between about 10 micrometres and about 100 micrometres. The filaments may give rise to capillary action in the interstices, so that liquid aerosol-forming substrate is drawn into the interstices, thereby increasing the contact area between the heater assembly and the liquid aerosol-forming substrate.

The electrically conductive filaments may form a mesh of size between about 160 Mesh US and about 600 Mesh US (+/−10%) (that is, between about 160 and about 600 filaments per inch (+/−10%)). The width of the interstices may be between about 75 micrometres and about 25 micrometres. The percentage of open area of the mesh, which is the ratio of the area of the interstices to the total area of the mesh, may be between about 25 percent and about 56 percent. The mesh may be formed using different types of weave or lattice structures. The electrically conductive filaments may be an array of filaments arranged parallel to one another.

The electrically conductive filaments may have a diameter of between about 8 micrometres and about 100 micrometres (e.g., between about 8 micrometres and about 50 micrometres, between about 8 micrometres and about 39 micrometres).

The resistive heating mesh may cover an area of less than or equal to about 25 square millimetres. The resistive heating mesh may be rectangular. In another instance, the resistive heating mesh may be square. The resistive heating mesh may have dimensions of about 5 millimetres by about 2 millimetres.

The electrically conductive filaments may comprise any suitable electrically conductive material. Suitable materials include but are not limited to semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal®, is a registered trade mark of Titanium Metals Corporation. The filaments may be coated with one or more insulators. The materials for the electrically conductive filaments may be 304, 316, 304L, and 316L stainless steel, and graphite.

The electrical resistance of the resistive heating mesh may be between about 0.3 and about 4 Ohms. For instance, the electrical resistance of the mesh may be between about 0.5 and about 3 Ohms (e.g., about 1 Ohm).

In example embodiments in which the electric heater comprises a resistive heating coil, the pitch of the coil may be between about 0.5 millimetres and about 1.5 millimetres (e.g., about 1.5 millimetres). The pitch of the coil means the spacing between adjacent turns of the coil. The coil may comprise fewer than six turns (e.g., fewer than five turns). The coil may be formed from an electrically resistive wire having a diameter of between about 0.10 millimetres and about 0.15 millimetres (e.g., about 0.125 millimetres). The electrically resistive wire may be formed of 904 or 301 stainless steel. Examples of other suitable metals include titanium, zirconium, tantalum and metals from the platinum group. Examples of other suitable metal alloys include, Constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. The resistive heating coil may also comprise a metal foil, such as an aluminium foil, which is provided in the form of a ribbon.

The aerosol-generating system may comprise a mouthpiece. The mouthpiece may form part of the cartridge. The mouthpiece may be formed separately from the cartridge and configured for attachment to at least one of the cartridge and the vaporiser section. The mouthpiece comprises a mouthpiece air outlet configured for fluidic communication with the cartridge air outlet during use.

The power supply may comprise a battery. For example, the power supply may be a nickel-metal hydride battery, a nickel cadmium battery, or a lithium based battery, for example a lithium-cobalt, a lithium-iron-phosphate or a lithium-polymer battery. The power supply may alternatively be another form of charge storage device such as a capacitor. The power supply may require recharging and may have a capacity that allows for the storage of enough energy for use of the aerosol-generating device with more than one cartridge.

The power supply section comprises a controller for controlling the supply of electrical power from the power supply to the electric heater.

FIGS. 1 to 5 show an aerosol-generating system 10 according to an example embodiment. The aerosol-generating system comprises a power supply section 12 connected to a vaporiser section 14, and a cartridge 16 separate from the power supply section 12 and the vaporiser section 14. The vaporiser section 14 comprises a vaporiser housing 18 defining a cavity 20 for receiving an upstream end of the cartridge 16.

The power supply section 12 comprises a system air inlet 22 for admitting air into the power supply section 12, a controller 24, and a power supply 26.

The vaporiser section 14 comprises a vaporiser air inlet 27 for receiving air from the power supply section 12, an airflow passage 28 in fluidic communication with the vaporiser air inlet 27 at its upstream end, and a vaporiser air outlet 30 in fluidic communication with the downstream end of the airflow passage 28. The vaporiser air outlet 30 has a semi-circular shape and is formed by a wall portion 31 of the vaporiser housing 18, the wall portion 31 also forming an upstream end wall of the cavity 20.

The vaporiser section 14 further comprises a liquid aerosol-forming substrate 32 sorbed into an annular porous carrier material 34 positioned outside of the airflow passage 28. A capillary wick 36 comprises first and second ends positioned in contact with the porous carrier material 34 and a central portion positioned within the airflow passage 28. Liquid aerosol-forming substrate 32 is wicked by capillary action along the capillary wick 36 from the porous carrier material 34 to the central portion of the capillary wick 36.

The vaporiser section 14 also comprises an electric heater 38 comprising a resistive heating coil wound around the central portion of the capillary wick 36. During operation of the aerosol-generating system 10, the controller 24 controls a supply of electrical energy from the power supply 26 to the electric heater 38 to heat and vaporise liquid aerosol-forming substrate 32 from the central portion of the capillary wick 36.

The cartridge 16 comprises a cartridge housing 40 defining a cartridge air inlet 42 and a cartridge air outlet 44. The cartridge air inlet 42 has a semi-circular shape and is formed by an upstream wall portion 45 of the cartridge housing 40.

A solid aerosol-forming substrate 46 is positioned within the cartridge housing 40 between the cartridge air inlet 42 and the cartridge air outlet 44. Mesh filters 48 may extend across the cartridge air inlet 42 and the cartridge air outlet 44 to retain the solid aerosol-forming substrate 46 in the cartridge housing 40. A mouthpiece 50 is formed at a downstream end of the cartridge 16, the mouthpiece 50 having a mouthpiece air outlet 52 in fluidic communication with the cartridge air outlet 44.

During use of the aerosol-generating system 10, air is drawn into the system through the system air inlet 22, through the vaporiser air inlet 27 and into the airflow passage 28 where vaporised liquid aerosol-forming substrate 32 is entrained in the airflow. The airflow then flows through the vaporiser air outlet 30, into the cartridge 16 via the cartridge air inlet 42 and through the solid aerosol-forming substrate 46 where volatile compounds from the solid aerosol-forming substrate 46 are entrained in the airflow. The airflow then flows through the cartridge air outlet 44 and out of the aerosol-generating system 10 through the mouthpiece air outlet 52 to deliver the vaporised liquid aerosol-forming substrate 32 and the volatile compounds from the solid aerosol-forming substrate 46.

Figure 3:
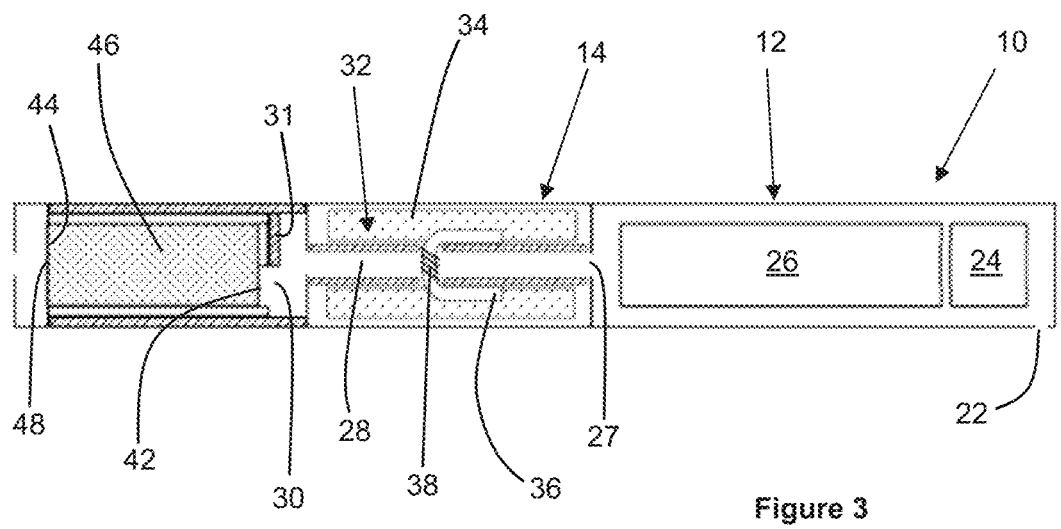
FIGS. 3 to 5 are cross-sectional views of the aerosol-generating system of FIG. 1 with the cartridge inserted into the cavity in different rotational orientations.
Figure 4:
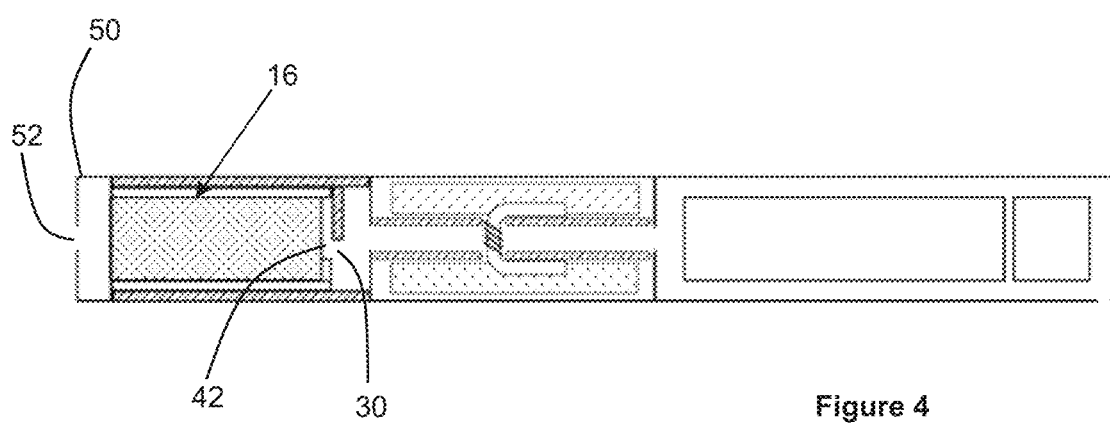
Figure 5:
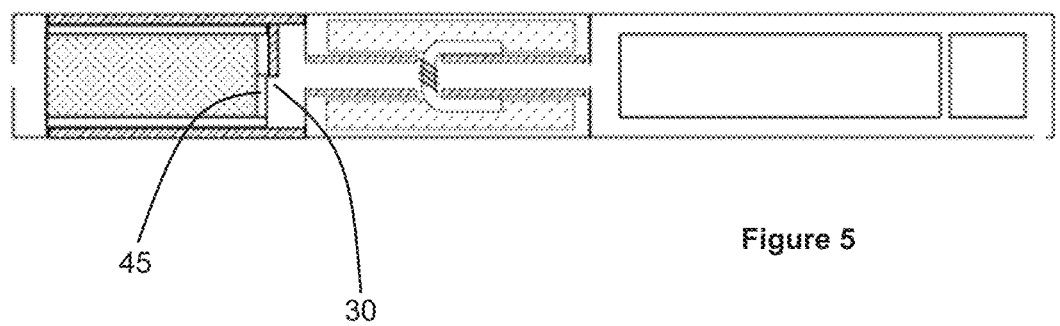

To vary the airflow through the aerosol-generating system 10, for example to vary the resistance to draw of the aerosol-generating system 10, the rotational orientation of the cartridge 16 can be varied with respect to the vaporiser section 14. As shown in FIGS. 3 to 5, which each show a different rotational orientation of the cartridge 16, varying the rotational orientation of the cartridge 16 varies the amount of overlap between the semi-circular vaporiser air outlet 30 and the semi-circular cartridge air inlet 42. FIG. 3 illustrates a rotational orientation in which there is complete overlap between the vaporiser air outlet 30 and the cartridge air inlet 42, which provides the minimum resistance to draw. FIG. 4 illustrates a rotational orientation in which there is a partial overlap between the vaporiser air outlet 30 and the cartridge air inlet 42, which increases the resistance to draw when compared to the rotational orientation of FIG. 3. FIG. 5 illustrate a rotational orientation in which there is no overlap between the vaporiser air outlet 30 and the cartridge air inlet 42 so that the upstream wall portion 45 of the cartridge housing 40 obstructs the vaporiser air outlet 30. Therefore, in the rotational orientation shown in FIG. 5, airflow through the aerosol-generating system 10 may be hindered or prevented, which may be desirable when the aerosol-generating system 10 is not in use.

To provide an indication of the relative rotation of the cartridge 16 with respect to the vaporiser section 14, a first indicium 62 is provided on the cartridge housing 40, and a second indicium 64 is provided on the vaporiser housing 18.

Figure 6:
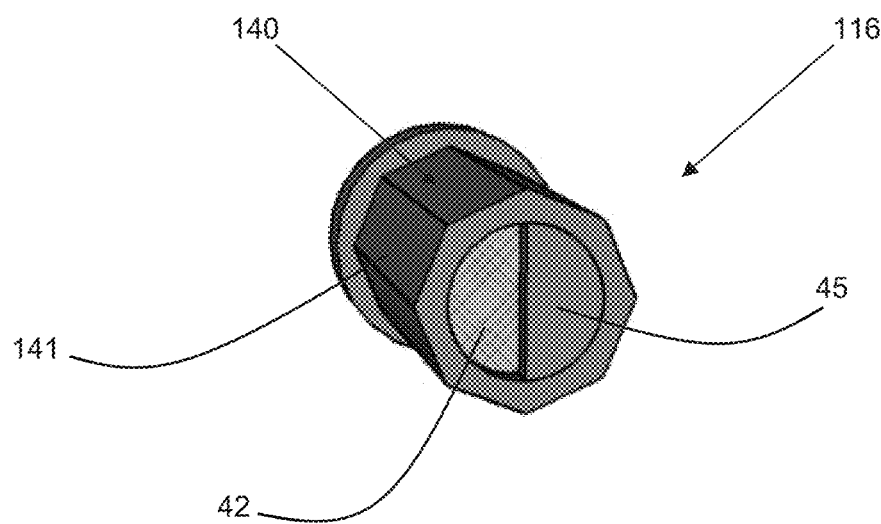
FIG. 6 is a perspective view of a cartridge according to an example embodiment.

FIG. 6 shows an alternative cartridge 116 according to an example embodiment. The cartridge 116 is similar to the cartridge 16 shown in FIGS. 1 to 5, and like reference numerals are used to designate like parts.

Cartridge 116 differs from cartridge 16 by the shape of the cartridge housing 140. In the example embodiment shown in FIGS. 1 to 5, the cartridge housing 40 has a circular cross-sectional shape so that the cartridge 16 can be inserted into the cavity 20 in any rotational orientation. In the example embodiment shown in FIG. 6, the cartridge 116 comprises a cartridge housing 140 having a polygonal cross-sectional shape defining a plurality of planar faces 141. The polygonal shape of the cartridge housing 140 restricts the rotational orientation of the cartridge 116 with respect to a vaporiser section of an aerosol-generating system.

Figure 7:
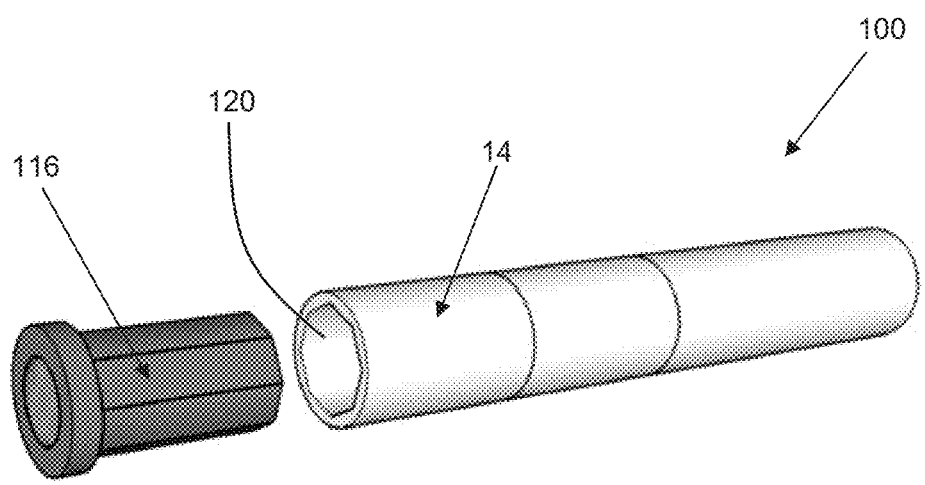
FIG. 7 is a perspective view of an aerosol-generating system comprising the cartridge of FIG. 6.

FIG. 7 shows an aerosol-generating system 100 comprising the cartridge 116. The aerosol-generating system 100 is similar to the aerosol-generating system 10 shown in FIGS. 1 to 5, and like reference numerals are used to designate like parts.

The aerosol-generating system 100 differs from the aerosol-generating system 10 by the shape of the cavity 120. In particular, the cavity 120 has a polygonal cross-sectional shape that matches the polygonal cross-sectional shape of the cartridge housing 140. The polygonal shape of the cavity restricts the rotational orientation of the cartridge 116 with respect to the vaporiser section 14 to a plurality of discrete rotational orientations. This arrangement allows a choice between a plurality of desired or predetermined rotational orientations each corresponding to a desired or predetermined amount of overlap between the vaporiser air outlet 30 and the cartridge air inlet 42.

Figure 8:
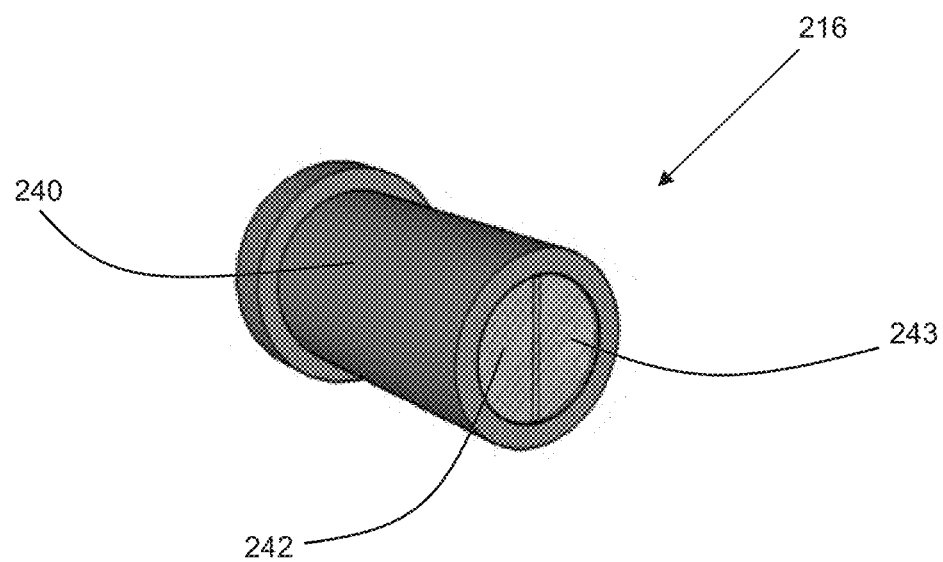
FIG. 8 is a perspective view of another cartridge according to an example embodiment.
Figure 9:
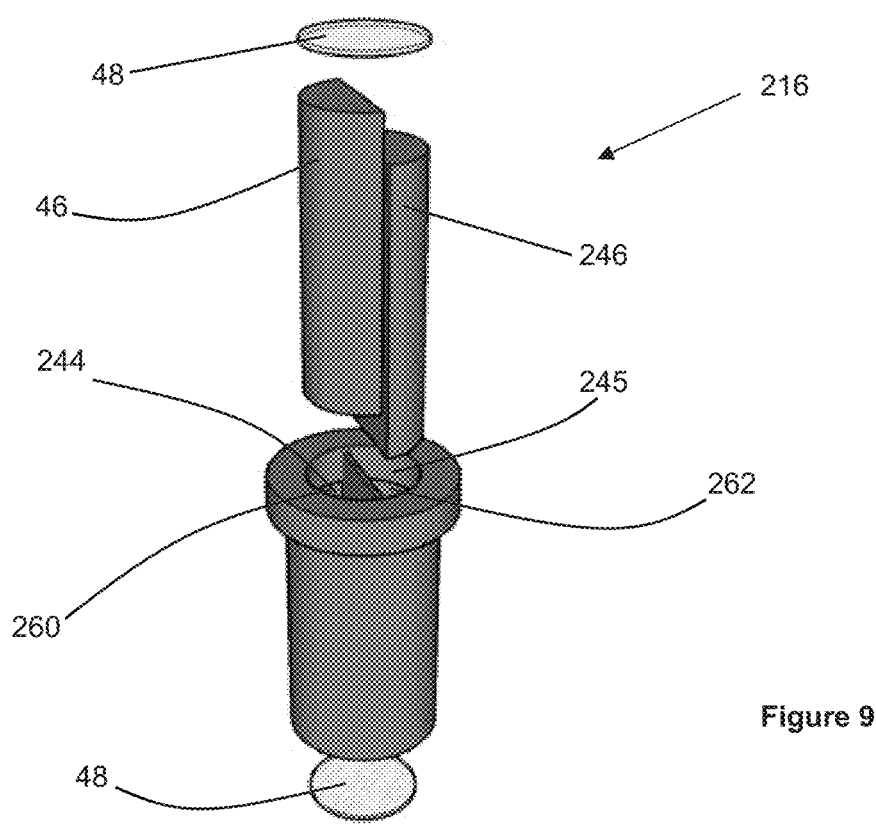
FIG. 9 is an exploded view of the cartridge of FIG. 8.

FIGS. 8 and 9 show a cartridge 216 according to an example embodiment. The cartridge 216 is similar to the cartridge 16 shown in FIGS. 1 to 5, and like reference numerals are used to designate like parts. The cartridge 216 may be used with the power supply section 12 and the vaporiser section 14 shown in FIGS. 1 to 5.

Cartridge 216 differs from cartridge 16 by the shape of the cartridge housing 240. In the example embodiment shown in FIGS. 1 to 5, the cartridge housing 40 defines a single compartment in which the solid aerosol-forming substrate 46 is positioned. In the example embodiment shown in FIGS. 8 and 9, the cartridge housing 240 defines a first compartment 260 in which the solid aerosol-forming substrate 46 is positioned and a second compartment 262 in which a second aerosol-forming substrate 246 is positioned. The second aerosol-forming substrate 246 may be different from the solid aerosol-forming substrate 46 and the liquid aerosol-forming substrate 32.

The cartridge air inlet of the cartridge 216 comprises a first cartridge air inlet 242 in fluidic communication with an upstream end of the first compartment 260 and a second cartridge air inlet 243 in fluidic communication with an upstream end of the second compartment 262. The cartridge air outlet of the cartridge 216 comprises a first cartridge air outlet 244 in fluidic communication with a downstream end of the first compartment 260 and a second cartridge air outlet 245 in fluidic communication with a downstream end of the second compartment 262. During use, the rotational orientation of the cartridge 216 with respect to the vaporiser section 14 may be varied to vary the amount of overlap between the vaporiser air outlet 30 and each of the first cartridge air inlet 242 and the second cartridge air inlet 243. Therefore, varying the rotational orientation of the cartridge 216 with respect to the vaporiser section 14 allows the relative amount of airflow through each of the first and second compartments 260, 262 to be varied.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

The invention claimed is:

1. An aerosol-generating system comprising:
a cartridge comprising a cartridge housing containing a solid aerosol-forming substrate, the cartridge housing defining a first cartridge air inlet, a second cartridge air inlet, and a cartridge air outlet, the first cartridge air inlet and the second cartridge air inlet extending through a cartridge wall portion of the cartridge housing;

a vaporiser section configured to receive the cartridge, the vaporiser section comprising a vaporiser housing containing an electric heater and a liquid aerosol-forming substrate, the vaporiser housing defining a vaporiser air inlet and a vaporiser air outlet, the vaporiser air outlet extending through a vaporiser wall portion of the vaporiser housing, the cartridge wall portion abutting the vaporiser wall portion when the cartridge is received within the vaporiser section, the cartridge configured to be rotatable with respect to the vaporiser section to vary an amount of overlap between the vaporiser air outlet and each of the first cartridge air inlet and the second cartridge air inlet; and a power supply section comprising a power supply configured to supply electrical power to the electric heater.

2. The aerosol-generating system according to claim 1, wherein the vaporiser housing defines a cavity configured to receive an upstream end of the cartridge housing.

3. The aerosol-generating system according to claim 2, wherein the cartridge wall portion is an upstream end wall of the cartridge housing, and the vaporiser wall portion is an upstream end wall of the cavity.

4. The aerosol-generating system according to claim 2, wherein the upstream end of the cartridge housing and the cavity each have a circular cross-sectional shape.

5. The aerosol-generating system according to claim 2, wherein the upstream end of the cartridge housing and the cavity each have a polygonal cross-sectional shape.

6. The aerosol-generating system according to claim 1, wherein each of the vaporiser air outlet, the first cartridge air inlet, and the second cartridge air inlet has a semi-circular shape.

7. The aerosol-generating system according to claim 1, wherein the cartridge housing defines a first compartment and a second compartment, the solid aerosol-forming substrate is within the first compartment, the first cartridge air inlet is in fluidic communication with the first compartment, and the second cartridge air inlet is in fluidic communication with the second compartment.

8. The aerosol-generating system according to claim 7, wherein the cartridge further comprises a second aerosol-forming substrate within the second compartment.

9. The aerosol-generating system according to claim 8, wherein the second aerosol-forming substrate comprises a flavourant.

10. The aerosol-generating system according to claim 1, wherein the cartridge is configured so that the amount of overlap between the vaporiser air outlet and the first cartridge air inlet increases as the amount of overlap between the vaporiser air outlet and the second cartridge air inlet decreases.

11. The aerosol-generating system according to claim 7, wherein each of the vaporiser air outlet, the first cartridge air inlet, and the second cartridge air inlet has a semi-circular shape.

12. The aerosol-generating system according to claim 1, further comprising:
   a first indicium on an outer surface of the cartridge housing; and
   a second indicium on an outer surface of the vaporiser housing,
   wherein the first indicium and the second indicium are configured to cooperate to indicate a rotational orientation of the cartridge with respect to the vaporiser section.

13. The aerosol-generating system according to claim 1, wherein the solid aerosol-forming substrate comprises tobacco.

14. The aerosol-generating system according to claim 1, wherein the liquid aerosol-forming substrate comprises a nicotine-containing liquid.

* * * * *